United States Patent [19]
Walker et al.

[11] Patent Number: 5,883,370
[45] Date of Patent: Mar. 16, 1999

[54] AUTOMATED METHOD FOR FILLING DRUG PRESCRIPTIONS

[75] Inventors: Ray A. Walker, Eugene, Oreg.; Marguerite E. Blackman, Meridian, Id.

[73] Assignee: PSC Inc., Webster, N.Y.

[21] Appl. No.: 658,281

[22] Filed: Jun. 5, 1996

Related U.S. Application Data

[60] Provisional application No. 60/000,061 Jun. 8, 1995.

[51] Int. Cl.$^6$ .............................. G06F 17/00; G07F 11/00
[52] U.S. Cl. ........................... 235/375; 235/462; 235/472
[58] Field of Search ...................................... 235/462, 375, 235/472

[56] References Cited

U.S. PATENT DOCUMENTS

| | | | |
|---|---|---|---|
| 3,921,196 | 11/1975 | Patterson | 235/462 |
| 4,476,381 | 10/1984 | Rubin | 235/375 |
| 4,835,372 | 5/1989 | Gombrich et al. | 235/375 |
| 4,857,716 | 8/1989 | Gombrich et al. | 235/462 |
| 4,918,604 | 4/1990 | Baum | 364/413.01 |
| 4,958,280 | 9/1990 | Pauly et al. | 364/403 |
| 5,208,762 | 5/1993 | Charhut et al. | 364/478 |
| 5,337,919 | 8/1994 | Spaulding et al. | 221/2 |
| 5,401,059 | 3/1995 | Ferrario | 283/67 |
| 5,451,760 | 9/1995 | Renvall | 235/462 |
| 5,542,420 | 8/1996 | Goldman et al. | 128/630 |
| 5,597,995 | 1/1997 | Williams et al. | 235/375 |
| 5,713,485 | 2/1998 | Liff et al. | 221/2 |
| 5,713,487 | 2/1998 | Coughlin | 221/2 |
| 5,762,235 | 6/1998 | Coughlin | 221/6 |

*Primary Examiner*—Anita Pellman Gross
*Assistant Examiner*—Douglas X. Rodriguez
*Attorney, Agent, or Firm*—Lyon & Lyon LLP

[57] ABSTRACT

An automated prescription filling system which assists the physician in providing a prescription and/or assists he pharmacist in filling a prescription in which the physician enters prescription information into his/her computer by which a bar coded prescription may be printed out. The prescription printed out includes a bar code containing all pertinent information including drug specification, dose strength, taking instructions, physician identification as well as corresponding human-readable typed information. The patient takes the prescription into the pharmacy and the pharmacist fills the prescription either in the conventional fashion since the prescription contains all the necessary information in typed form, or the pharmacist scans the bar code(s) and the prescription is automatically entered into pharmacy computer. The pharmacist then selects the matching drug from the shelf container and scans the NDC (National Drug Code) bar-code on the container. The system confirms a match between the NDC and the prescription and then permits issue of the prescription, printing out a vial label.

13 Claims, 5 Drawing Sheets

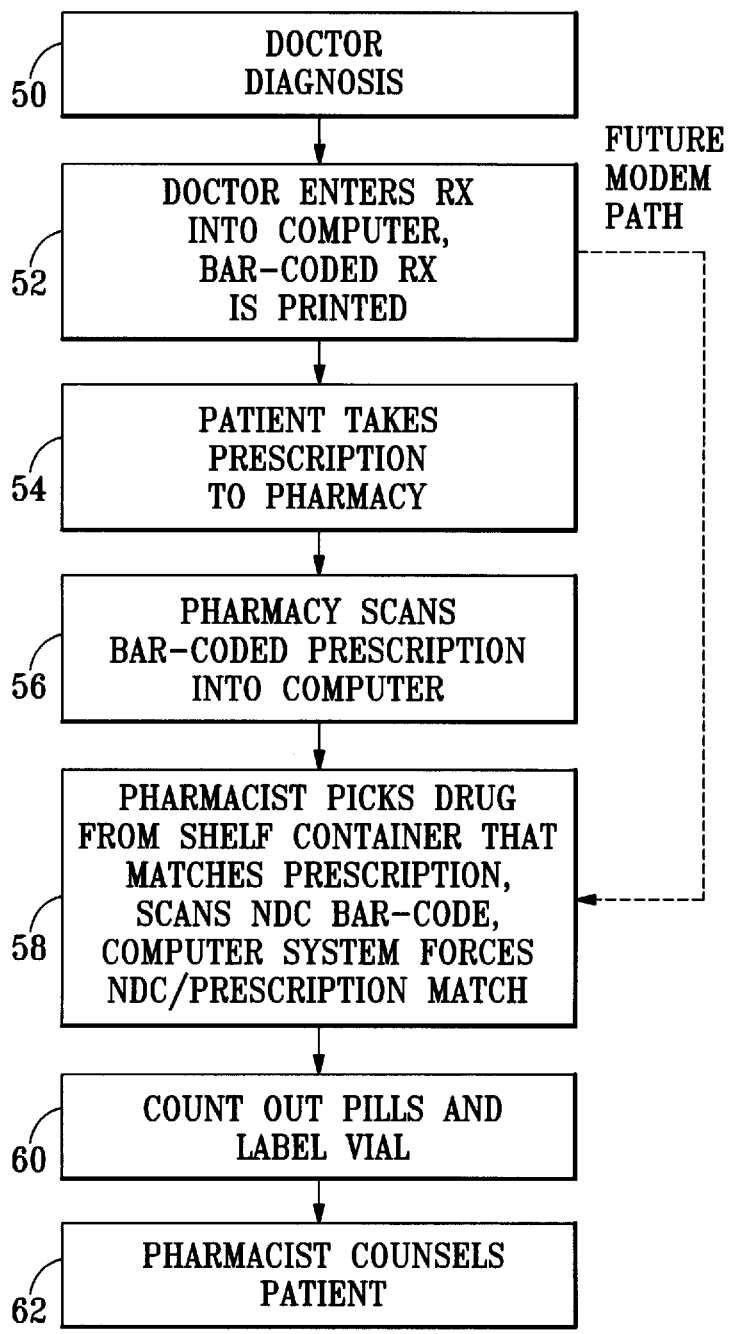

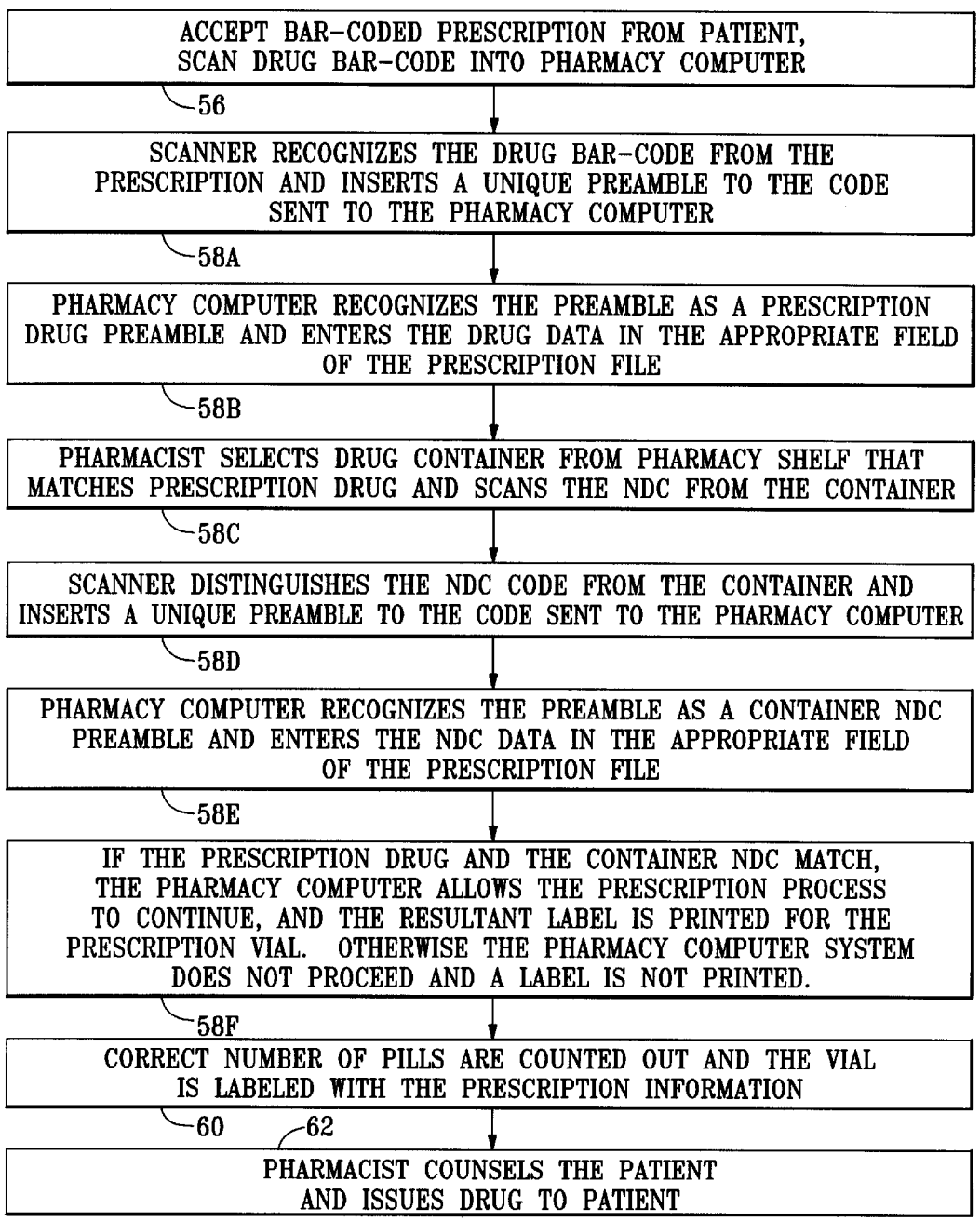

AUTOMATED METHOD FOR FILLING DRUG PRESCRIPTIONS

RELATED APPLICATION DATA

This application is a continuing application of provisional application Ser. No. 60/000,061 filed Jun. 8, 1995.

BACKGROUND OF THE INVENTION

The field of the present invention relates to an automated verification system and more specifically to a bar coded system of verification for filling pharmacy prescriptions.

FIG. 1 depicts a flow diagram of a typical physician-to-pharmacy prescription system. The physician makes the diagnosis (step 10) and then writes out a prescription (step 12) which the patient takes to the pharmacy (step 14). The pharmacist interprets the physician's prescription (step 16) and then selects the drug from the shelf container containing the appropriate drug (step 18), fills the vial with the appropriate quantity of the drug and labels the vial (step 20). The pharmacist completes the transaction by counseling the patient (step 22). Two steps in this system are prone to errors that are correctable by an automated verification system. First, the step in which the pharmacist interprets the prescription (step 16) requires the pharmacist to correctly render the hand-written directions of the doctor. This step may be prone to error because of the element of human error when reading the doctor's hand-written prescription. Moreover, doctors may write somewhat illegibly, thereby increasing the possibility of a mis-read. A second step prone to error is when the pharmacist picks drug from inventory on the pharmacy shelf that matches the prescription (step 18). After the prescription from the doctor is rendered, the corresponding drug is located from the inventory in the pharmacy to fill the prescription. If both the rendering of the doctors intended drug and the subsequent selection of that drug from the pharmacy inventory are performed correctly, the physician-to-pharmacy prescription system has functioned properly.

Electronic prescription transmission from the doctor's office to the pharmacies is now being worked on by a consortium of drug stores, pharmacy software suppliers, and other pharmacy industry parties, however, these systems do not verify the match between the doctor's prescription and the drug selected from the pharmacy's inventory to fill the prescription and the filled prescription container handed to the customer.

SUMMARY OF THE INVENTION

The present invention is directed to an automated prescription filling system which assists the physician in providing a prescription and/or assists the pharmacist in filling a prescription. The physician enters prescription information into his/her computer by which a bar coded prescription may be printed out. The prescription printed out include's a bar code containing all pertinent information including drug specification, dose strength, taking instructions, physician identification as well as typed information. The patient takes the prescription into the pharmacy and the pharmacist fills the prescription either in the conventional fashion since the prescription contains all the necessary information in typed form, or the pharmacist scans the bar code(s) and the prescription is automatically entered into pharmacy computer. The pharmacist then selects the matching drug from the shelf container and scans the NDC (National Drug Code) bar-code on the container. The system confirms a match between the NDC and the prescription and then prints out a vial label.

BRIEF DESCRIPTION OF THE DRAWINGS

FIG. 3 is a flow diagram of a physician-to-pharmacy prescription system according to a alternate embodiment of the present invention;

FIG. 4 is a detailed flow chart of the physician-to-pharmacy prescription system of FIG. 3;

DETAILED DESCRIPTION OF THE PREFERRED EMBODIMENTS

Preferred embodiments of the present invention will now be described with reference to the drawings.

Figure 2:
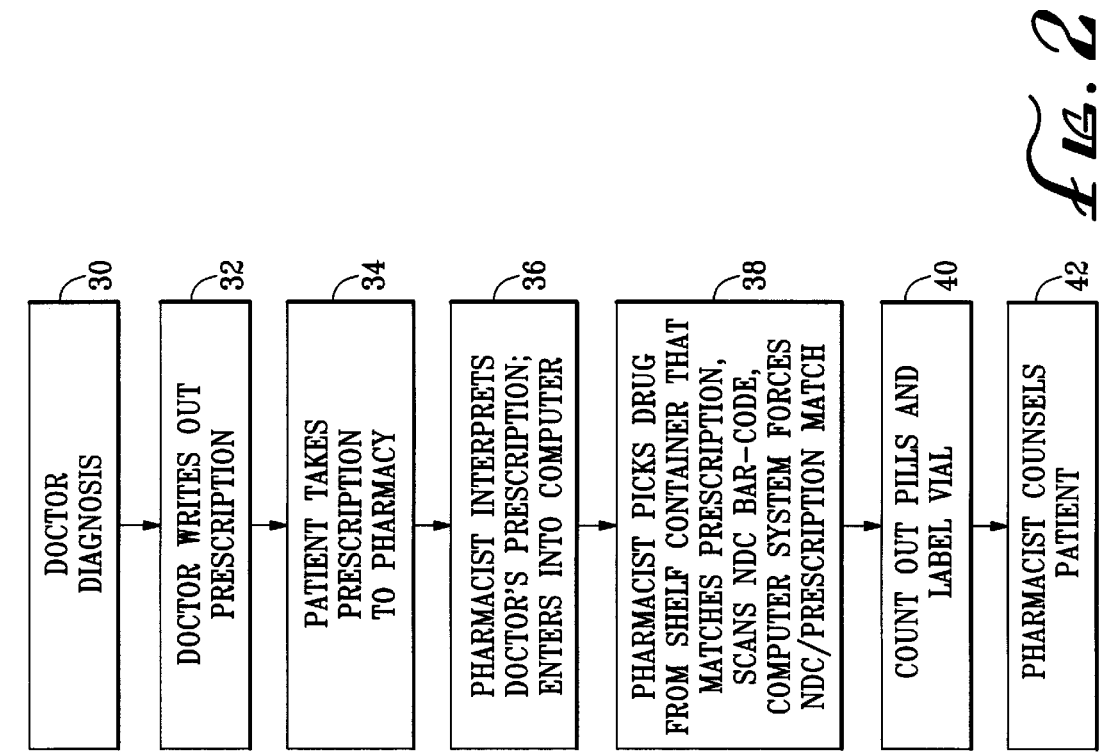
FIG. 2 is a flow diagram of a physician-to-pharmacy prescription system according to a preferred embodiment of the present invention.
Figure 1:
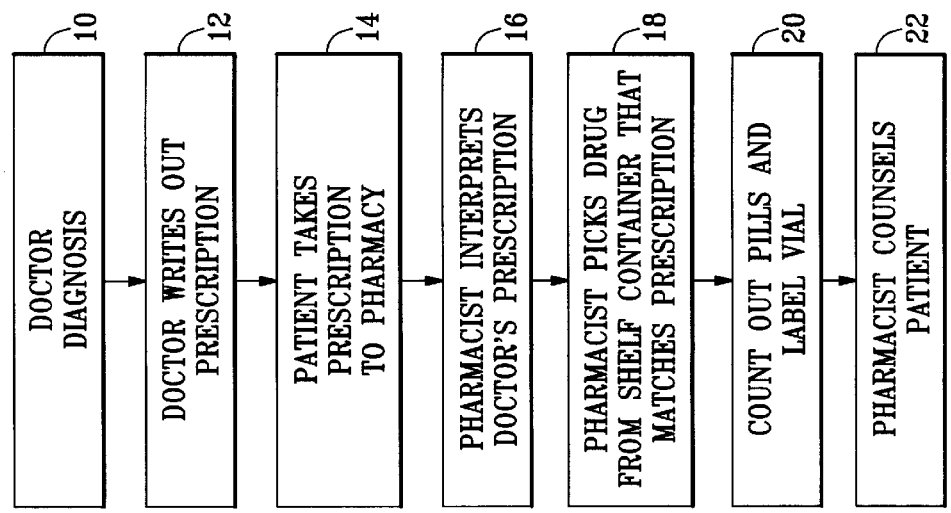
FIG. 1 is a flow diagram of a typical physician-to-pharmacy prescription system.

A general description of a preferred embodiment of the verification system is depicted in FIG. 2. The physician makes the diagnosis (step 30) and then writes out a prescription slip (step 32) which the patient takes to the pharmacy (step 34). The pharmacist interprets the physician's prescription from the slip and enters the pertinent prescription into the computer (step 36). The pharmacist then selects the drug from the shelf container containing the drug that matches prescription, scans the NDC bar-code and the system confirms a match between the NDC and the prescription (step 38). The pharmacist then fills the vial with the appropriate quantity of the drug, labels the vial (step 40) and completes the transaction by counseling the patient (step 42).

This system requires a verification match, but the pharmacist still must accurately render the doctor's written prescription (step 36). The pharmacist, with the use of the verification system, will verify that the container selected from the pharmacy inventory matches the doctors prescription by requiring the scan of the NDC bar code label on the selected container to be scanned and to match the prescription (step 38), which the pharmacist will render from the doctor's written prescription. A detailed description of the bar coded prescription system in the pharmacy alone follows.

In the modern pharmacy, a computer is utilized to aid in the filling and billing of prescriptions. The pharmacist, or an assistant, enters the prescribed drug and related information, still based upon their rendering of the doctor's hand written prescription slip into the computer. The selection process is typically facilitated by a menu driven alphabetical list which expedites the selection and entry process. After this entry is made, the pharmacist will fill the prescription, however, human error can enter at this step because the pharmacist must manually select the drug from the pharmacy's inventory (or must select the proper dose strength of the drug, which will often be in a separate container).

In the preferred embodiment according to FIG. 2, the likelihood of human error is diminished because once the prescription has been entered into the pharmacy computer (step 36), the pharmacist may fill the prescription slip by selecting and scanning the matching NDC label on the container (step 38). The pharmacy scanner will be linked to the pharmacy computer, so a match may be required before processing may continue, such as, producing a vial label for the prescription container (step 40), proceeding to billing, or filling another prescription. Alternatively, an error signal may be activated which notifies the pharmacist and/or the store computer and/or another display on the pharmacy computer which requires some sort of corrective action be taken before the error signal is discontinued.

It is critical that the computer can distinguish between the entry of the prescription slip entry and the scanning of the NDC bar code label, otherwise, either could be entered twice as a means of verification. There are a number of solutions to this problem including: enabling the computer to distinguish between the two types of entered data (prescription slip data and the bulk drug container); connecting the scanner to a separate (logically or with hardware) port of the computer; use of the scanner in a wedge configuration and modification of the program to recognize the scanned data distinctly from the manually keyed data; or make the scanner context sensitive based upon where the data is sent or what additional data is sent with the scanned data.

Another preferred embodiment would be more fully automated and would remove the step of interpreting or rendering the doctor's hand written prescription. This embodiment is generally depicted in FIG. 3, and a detailed flow diagram is illustrated in FIG. 4. The physician makes the diagnosis (step 50) and then writes out a prescription by entering it into a computer which prints out a bar-coded prescription (step 52) which the patient takes to the pharmacy (step 54). In this second embodiment, the patient brings the prescription slip to the pharmacy just like the hand-written prescription, however, the prescription slip of this embodiment includes a bar code (see FIGS. 5 and 6 and description below). Instead of only reading or interpreting the doctor's prescription and manually entering the prescription into the pharmacy computer, the pharmacist simply scans the prescription slip bar code(s) into the pharmacy computer (step 56). As in the first embodiment described above, a match would be required when selecting the proper NDC container from the pharmacy's inventory (step 58). Preferably, the scanner would use context-sensitive scanning capabilities based on information embedded in the bar code label on the NDC container and the bar coded prescription slip to distinguish between the two, so one bar code could not be entered twice to affect a match/verification and permit additional processing. Other means of making this distinction are discussed above. Alternatively, the scanner could be programmed to use any context-sensitive feature for the respective bar codes to add a unique preamble such that the pharmacy computer could distinguish the bar codes (step 58a), thereby precluding affected matches by scanning either the prescription or the NDC label twice. The pharmacy computer will distinguish the two bar-codes by their respective preambles or the embedded information in their bar codes or the context of their respective coded information, and the computer will therefore only allow entry of the NDC bar code label information or the doctor prescription bar coded data in the appropriate field in the pharmacy computer (step 58b).

In addition, upon scanning the bar code on the prescription slip presented by the patient, the pharmacy computer may also provide location information to direct the pharmacist to the proper shelf container corresponding to the information obtained from the prescription slip.

Following the identification of the desired prescription drug based upon the scanning of the bar coded prescription and pharmacy computer display thereof, the pharmacist will select the appropriate drug container from the pharmacy's inventory and scan the NDC bar-code on the container (step 58c). When the scanner encounters the inventory NDC bar-code, it may use context-sensitive scanning to attach a preamble to the bar-code data and when this message is sent to the pharmacy computer (step 58d), it stores the data in the corresponding field in the pharmacy computer (step 58e). The preamble or the other means for distinguishing the two bar codes may also be used to keep the pharmacy computer from mistaking these bar codes from for-sale items.

If the drug bar code scanned from the prescription and the NDC bar-code scanned from the pharmacy shelf container match, the pharmacy computer allows the process to continue and a label is printed for the filled prescription container and automated billing proceeds accordingly (step 58f). The pharmacist counts out the desired number of pills (or measures and prepares the prescription as required) and attaches the label to the prescription vial (step 60). In future systems these last two steps may be automated—even the selection of the NDC container could be automated. Though technologically feasible, these systems would have to demonstrate effectiveness and advantage in order to gain market acceptance.

If the bar codes from the prescription and the pharmacy inventory container do not match, the prescription process is stalled, and no label will be printed (step 58f).

In the final step in which the pharmacist counsels the patient and issues drug to patient (step 62) is required in many states for all new prescriptions while it is optional for refills. In any case, the consultation can be done with more confidence since the pharmacist knows that the critical steps of filling the prescription has been monitored and verified by the computer and obvious errors have been avoided. Moreover, the pharmacist can compare the printed prescription slip to the vial label to provide a final manual check.

Figure 5:
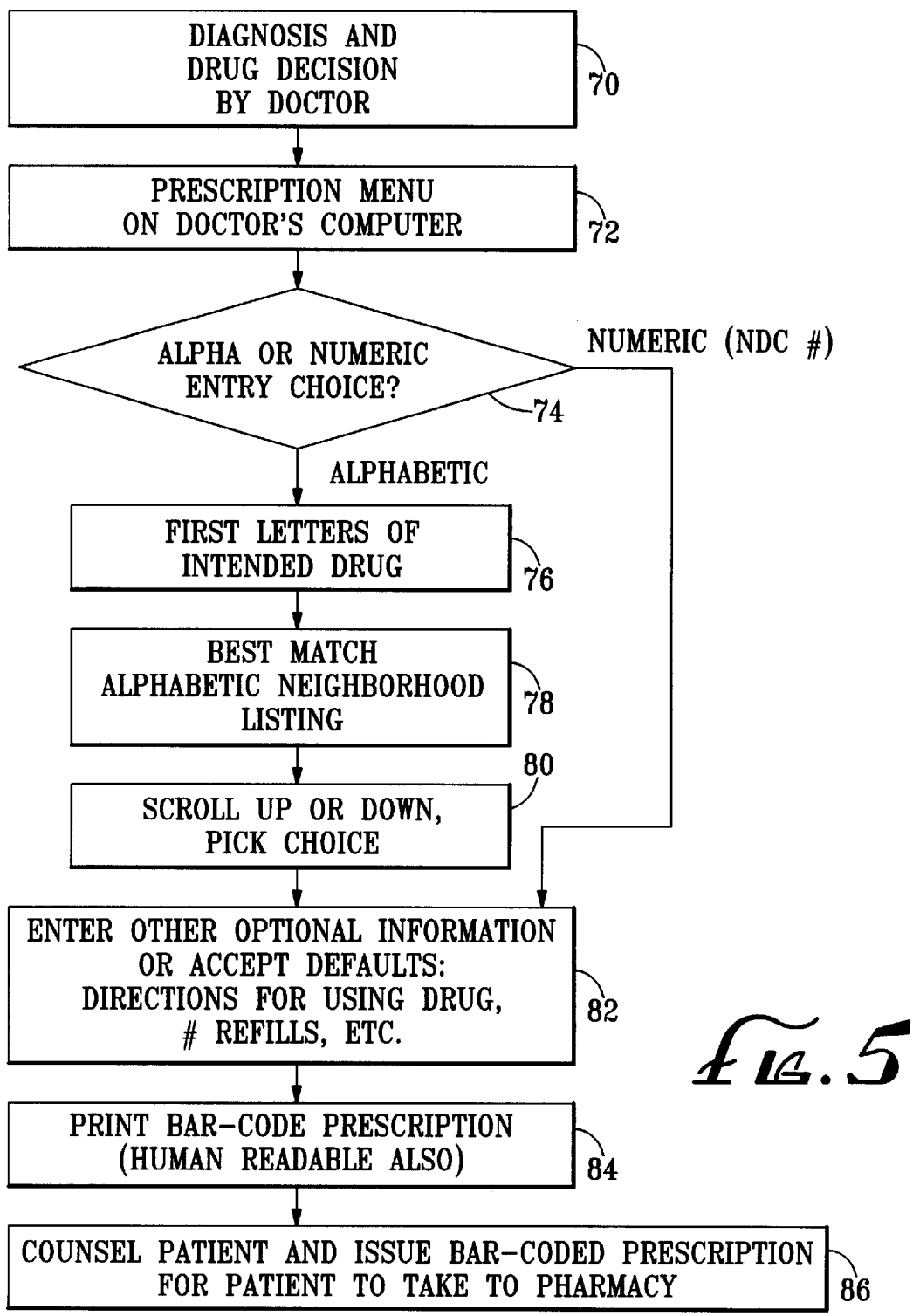
FIG. 5 is a flow chart describing the means by which the bar code may be generated at the doctor's office.

FIG. 5 depicts one means in which the bar code may be generated at the doctor's office. The diagnosis and drug selection by the doctor is done in the normal manner (step 70), however, instead of taking a pen to a prescription pad, the doctor may simply open her/his laptop or palmtop computer and go to the prescription menu to select a prescription drug (step 72).

The palmtop computer, or functional equivalent, may also be menu driven and user-friendly system similar to the pharmacy drug selection process described above which will facilitate and expedite the doctor's drug selection or the doctor may enter the drug by spelling it out or using a predesignated number. Necessary options e.g. directions for use, number of refills allowed without another prescription, etc. may also be entered. When the options desired are complete, the doctor will terminate the process with an appropriate key stroke (or mouse selection) and the associated bar-coded prescription slip will be printed out by the computer (step 84).

FIG. 5 illustrates an example input scheme. The physician is provided a choice to identify the drug by name (i.e. alpha numerically) or by numeric NDC number (step 74). If NDC # is chosen, the physician merely enters the code and system proceeds to step 82 for entry of additional information. If alphanumeric entry is chosen, the physician enters the first letters of the drug (step 76) and the system provides a listing at best match from those in memory (step (78). The physician then scrolls the listing and chooses the correct entry (step 80). Once the drug is chosen, the physician is prompted to either accept defaults, or enter other optional information such as dosage, instructions on use, number of refills permitted or the like (step 82). The physician can be provided with various warnings, side effects, harmful drug interactions, updated medical information on the drug, or even typical usages for the drug to assist the physician in confirming the proper drug choice has been made and is being prescribed. Once confirmed, the bar-code prescription slip is printed (step 84) and the physician can issue the prescription and counsel patient (step 86), possibly using the information provided by the system at step 82.

Figure 6:
FIG. 6 is an example of a prescription printout.

FIG. 6 illustrates an example prescription slip 90. The printout 90 may include a patient identification field 91; drug, dosage and quantity field 92; taking instruction field 93; number of refills field 94; physician signature space 95; date field 96; drug identification, dosage and quantity bar code 97; physician identification bar code 98. Confirmation printouts 99 of the bar codes may be provided over the codes themselves. The use of the bar codes (the bar codes containing the drug, dosage and quantity information) makes improper alteration by the patient difficult.

FIG. 3 also depicts an alternative means of entering the doctor's prescription into the pharmacy computer. The dotted line labeled "Future Modem Path" would enable the doctor to send the prescription directly to a particular pharmacy's computer, the hospital pharmacy, or the patient's pharmacy, thereby eliminating the need for the patient to handle the prescription—this automation may also removes a potential glitch in the prescription filling process—e.g. patients who lose the prescriptions or possibly try to alter them. The steps of filling the prescription and verifying that the proper NDC container was selected would be the same as described above.

The final step is for the doctor to counsel the patient about the prescription. It is noted that the patient is not required to take the prescription slip 90 to only pharmacies where the bar-code can be read by a scanner. Since the bar-code prescription slip 90 also has human-readable characters on it along with the bar-codes, the patient is free to take it to any pharmacy of their choosing. Pharmacies where scanners and appropriate systems are not available would fill the prescription by using the human-readable information in the normal manner, except that they would not have to read any poor hand writing of the doctor.

Since the doctor's computer has identification of the prescription, the computer system may include in its memory detailed information on the prescription drug (including for example standard directions for use of the drug, warnings, side effects, drug interaction, and/or allergic potential). The information may be outputted upon entry and used by the doctor to advise the patient or to consider when prescribing and/or printed out and provided to the patient.

It should be noted that generic drugs or replacement drugs would also be programmed to match certain prescriptions if the FDA and the doctor approved.

Thus, an automated drug prescription filling system has been shown and described. Though certain examples and advantages have been disclosed, further advantages and modifications may become obvious to one skilled in the art from the disclosures herein and the invention is not to be limited thereby except in the spirit of the claims that follow.

What is claimed is:

1. A method for automating prescription filling comprising the steps of inputting drug selection into a computer;

printing out a prescription slip with a prescription bar code which contains pertinent prescription information to enable filling of the prescription;

taking the prescription slip to a pharmacist; and having the pharmacist fill the prescription by scanning the prescription bar code on the prescription slip to obtain the pertinent prescription information, selecting a matching drug from a shelf container, scanning a container bar-code on the shelf container representing contents thereof, confirming a match between the container bar code and the pertinent prescription information in the prescription slip bar code and if a match is confirmed, printing out a vial label.

2. A method according to claim 1 wherein the pertinent prescription information contained in the prescription bar code includes: drug specification, dose strength, taking instructions, and physician identification.

3. A method according to claim 1 wherein the prescription slip also contains human-readable typed information corresponding to the pertinent prescription information.

4. A method according to claim 1 preventing filling of the prescription if a match is not confirmed between the container bar code and the pertinent prescription information in the prescription slip bar code.

5. A method according to claim 1 further comprising providing the prescription bar code on the prescription slip with complete information for filling the prescription.

6. A method for automating filling of a prescription from a physician, comprising the steps of obtaining a prescription from the physician;

inputting pertinent drug information from the prescription into a computer at a pharmacy;

selecting a matching drug from a shelf container;

scanning a container bar-code on the shelf container representing contents thereof;

confirming a match between the container bar code and the pertinent drug information from the prescription and if a match is confirmed, permitting filling of the prescription.

7. A method according to claim 6 preventing filling of the prescription if a match is not confirmed between the container bar code and the pertinent drug information inputted.

8. A method according to claim 6 further comprising the step of electronically transmitting the pertinent drug information from the physician to the pharmacy.

9. A method for automating prescription filling comprising the steps of inputting drug selection into a computer or terminal;

printing out a prescription slip with embedded information which is machine readable and contains complete prescription information to enable filling of the prescription;

taking the prescription slip to a pharmacist; and having the pharmacist fill the prescription by using a reader to obtain the embedded information on the prescription slip to obtain the pertinent prescription information, selecting a matching drug from a shelf container, using the reader to obtain embedded information from a label on the shelf container representing contents thereof, wherein the system confirms a match between the container label and the pertinent prescription information embedded on the prescription slip.

10. A method according to claim 9 further comprising filling a vial with a proper quantity of the matching drug, wherein the vial is prevented from being filled if a match is not confirmed.

11. A method according to claim 9 wherein the embedded information on the prescription slip comprises a bar code label readable by a bar code scanner and wherein the step of using a reader to obtain the embedded information comprises scanning the bar code label with the bar code scanner.

12. A method according to claim 9 wherein the prescription vial label is printed only if a match has been confirmed.

13. A method according to claim 9 wherein the prescription slip also contains human-readable typed information corresponding to the pertinent prescription information.

* * * * *